United States Patent [19]

Daniel

[11] 4,272,408
[45] Jun. 9, 1981

[54] STABLE MOLYBDENUM CATALYSTS FOR HIGH CONVERSION OF $C^3$ AND $C^4$ OLEFINS TO CORRESPONDING UNSATURATED ALDEHYDES AND ACIDS

[75] Inventor: Chelliah Daniel, Columbus, Ohio

[73] Assignee: Air Products and Chemicals, Inc., Allentown, Pa.

[21] Appl. No.: 133,045

[22] Filed: Mar. 24, 1980

Related U.S. Application Data

[63] Continuation-in-part of Ser. No. 952,177, Oct. 17, 1978, Pat. No. 4,212,767.

[51] Int. Cl.³ .................. B01J 27/14; B01J 27/24; B01J 27/02; B01J 27/06
[52] U.S. Cl. .................. 252/437; 252/435; 252/438; 252/439; 252/441
[58] Field of Search .............. 252/435, 437, 438, 439, 252/441, 454, 456, 458, 462

[56] References Cited

U.S. PATENT DOCUMENTS 4,212,767  7/1980  Daniel .................. 252/437 X

Primary Examiner—Delbert E. Gantz
Assistant Examiner—William G. Wright
Attorney, Agent, or Firm—Richard A. Dannells, Jr.; James C. Simmons; E. Eugene Innis

[57] ABSTRACT

A stabilized heteropoly molybdate catalyst precursor in calcined form and containing anionic molybdenum in defect state is surface impregnated with certain metal cations. The stabilized precursor is one obtained by incorporating into the reaction product of a molybdate and a soluble phosphate, silicate or arsenate, an aqueous chloride ion and a compound of phosphotungstate, silicotungstate, vanadium arsenate, silico-arsenate, phosphovanadate, or silicovanadate, followed by drying and calcining. During the chloride ion stabilization step other metals may be optionally incorporated in forming the stabilized precursor.

The obtained precursor is catalytically active in the conversion of the unsaturated aldehydes to the corresponding unsaturated carboxylic acids with or without incorporation of the metal cation during the chloride ion stabilization step. When the obtained calcined precursor is surface impregnated with a Group VIII metal cation, preferably cobalt and/or iron, and with a compound of selenium or tellurium, the resulting catalysts are highly active and are capable of direct conversion of $C_3$-$C_4$ monoolefins in a single step to the corresponding unsaturated carboxylic acids.

23 Claims, No Drawings

STABLE MOLYBDENUM CATALYSTS FOR HIGH CONVERSION OF C³ AND C⁴ OLEFINS TO CORRESPONDING UNSATURATED ALDEHYDES AND ACIDS

CROSS REFERENCE TO RELATED APPLICATIONS

This application is a continuation-in-part of application Ser. No. 952,177, filed Oct. 17, 1978, now U.S. Pat. No. 4,212,767

BACKGROUND OF THE INVENTION

1. Field of the Invention

The invention is directed to methods for the preparation of stable heteropoly molybdate catalysts and use of certain of the obtained catalysts particularly in the conversion of C₃ and C₄ olefins to their corresponding unsaturated aldehydes and unsaturated acids.

2. Description of the Prior Art

The preparation of acrylic acid from propylene and the preparation of methacrylic acid from isobutylene are generally carried out in two stages under independently selected conditions for each stage and most often employing different catalysts selected for each stage. In the first stage the olefin is catalytically oxidized to the aldehyde with the formation of possibly a small amount of the corresponding C₃ or C₄ unsaturated acid. The obtained aldehyde is converted to the acid in the second stage generally in the presence of a different catalyst. Among the better known commercial processes, the production of acrolein is effected by catalytic oxidation of propylene with oxygen over supported CuO catalyst at about 350° C.; or by air oxidation of propylene over BiO₃/MoO₃ catalyst at 300°–360° C. The oxidation of the acrolein formed by the foregoing or other processes is carried out in a second catalytic reactor generally at a temperature of about 250° C.

Numerous different catalysts have been proposed in the prior patented art for the conversion of acrolein and methacrolein to the corresponding unsaturated acis, more generally comprising metal molybdates and phosphomolybdates combined with various metal cations. Typical among such are U.S. Pat. Nos. 3,326,817; 3,865,873; 3,875,220; 3,882,047; 3,925,464; 3,976,888; 3,998,876; 4,000,088; 4,001,316; 4,017,423; 4,025,565; 4,035,262; 4,042,533; 4,042,625; 4,045,478; 4,051,179; 4,070,397; 4,072,708; 4,075,123; 4,075,124; and 4,075,244.

As an example of such prior art methods is that described in U.S. Pat. No. 3,965,163. As therein described, a solution of antimony trichloride in hydrochloric acid is combined with phosphomolybdic acid, and tungsten trioxide is then added to the obtained solution. The resulting mixture when dried and calcined forms a catalyst having the empirical formula $$Sb_1Mo_{12}W_1P_1O_{41.5}$$

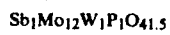

U.S. Pat. No. 4,034,008 discloses the oxidation of alpha, beta unsaturated monoolefins with molecular oxygen to produce the unsaturated acid as well as the unsaturated aldehyde. The reaction is carried out in the presence of steam at about 350°–450° C. over catalyst comprising a major portion of molybdena associated with oxides of bismuth, iron, silica, nickel or cobalt, antimony or ruthenium and optionally containing chloride ion. At best only about 1 to 2 parts by weight of acrylic acid are obtained along with about 13 to 15 parts acrolein or about 1 to 2.65 parts acrylic acid with 16 to 19 parts acrolein.

SUMMARY OF THE INVENTION

In the aforesaid parent application Ser. No. 952,177 filed Oct. 17, 1978 now U.S. Pat. No. 4,212,767, a method is described for preparing molybdate catalysts of high purity and stabilized activity by utilizing a chloride ion stabilization step (CIS) wherein a water-soluble non-metallic molybdate is combined with a water-soluble compound of an element from the group consisting of silicon, phosphorus and arsenic in aqueous solution and there is added to this mixture an aqueous chloride ion and a compound selected from the group consisting phosphotungstate, silicotungstate, vanadium arsenate, silico-arsenate, phosphovanadate, silicovanadate or mixtures of these. By drying and calcining the resulting reaction product, a stable, active oxidation catalyst is obtained having an empirical formula $$Y_wMo_xA_yO_z \qquad (I)$$

wherein Y is phosphorus, arsenic, silicon or mixtures thereof,

A is tungsten, vanadium, arsenic (when Y is not arsenic), or mixtures thereof, and w, x, y, and z are numerical quantities defining the relative molar proportion of these elements in the catalyst.

As disclosed in said parent application the activity of such catalysts can be further enhanced by incorporating a metal cation therein during the chloride ion stabilization step, resulting in a catalyst of the empirical formula $$X_uY_wMo_xA_yO_z \qquad (II)$$

wherein Y and A and the common subscripts are the same as in Formula I above, and X is one or more of the selected metal cations, and u is a number indicating the proportionate mole quantity of X present in the catalyst.

The catalysts prepared in accordance with the methods described in said prior parent application are advantageously useful in oxidizing unsaturated aldehydes such as acrolein and methacrolein respectively to acrylic and methacrylic acids.

In accordance with the present invention calcined molybdate catalysts prepared by utilizing the CIS step of said prior patent application are employed as precursors, into the surface of which one or more of certain metal cations are further incorporated, preferably including among these a Group VIII base metal. The preferred catalysts of the present invention comprise as the metal cation incorporated into the calcined molybdate catalyst precursor cobalt and/or iron optionally together with a non-metallic ion from Group VIA (selenium or tellurium). Catalysts of the present invention correspond to the empirical formula $$D_{1.5}E_{0.1}G_{0.5.4}P_{0.5.3}Mo_{10.12}L_{0.2}O_z \qquad (III)$$

wherein D can be one or more elements from the group iron, cobalt, nickel, copper, bismuth, chromium, tin, manganese antimony and lead;

E can be an alkaline earth metal such as magnesium, barium or strontium;

G can be silicon, tellurium, selenium or arsenic;

L is one or more elements from the group consisting of tungsten and vanadium, and z is the residual valence to satisfy the formula.

When the proportion of D is increased to above 3 and up to about 6, high yields of aldehyde are obtained in the conversion of olefins.

The preferred catalysts of the invention are those which are active in the one-step oxidative conversion of $C_3$ and $C_4$ monoolefins obtaining high yields of oxidized products including the corresponding unsaturated monocarboxylic acids as well as the corresponding unsaturated aldehydes. These preferred catalysts correspond to one of the empirical formulae $$M_{3-5}R_{2-3}P_{1.5-0.5}Mo_{20}O_z \quad (IV)$$

$$M_{1-3}R_{0.5-2}P_{1-1.5}W_{1-2}Mo_{10}O_z \quad (V)$$

$$M_{1-2}R_{1-3}P_{2-4}W_{1-3}Mo_{20}O_z \quad (VI)$$

wherein M comprises one or more metal cations, at least one of which is a base metal cation from Group VIII of the Periodic Table and preferably cobalt, iron or both of these, and R is at least one element from the group consisting of selenium and tellurium. The preferred catalysts of formulae IV, V, VI, are those in which the ratio of metal cation (M) to molybdenum is not more than about 3/10. With increase in proportion of metal cation highly active catalysts are obtained for conversion of olefins to unsaturated aldehydes but such catalysts lose activity and selectivity for direct one-step conversion of the olefin to the corresponding unsaturated carboxylic acid.

In the above formulae IV to VI part of the phosphorus may be replaced by silicon, arsenic or boron; the total content of phosphorus and such replacement falling within the indicated proportions. Also the tungsten in formuale V and VI may be partly replaced by vanadium.

DETAILED DESCRIPTION

Preparation of the Precursor

The precursors employed in preparing the final catalysts of the present invention are prepared employing the chloride ion stabilization step as described in aforesaid parent application Ser. No. 952,177. By utilizing such stabilization step, the need for precise pH control during the crucial stages of the preparation is avoided, and the obtained precursors themselves have high catalytic activity in oxidation of aldehydes to corresponding acids even without incorporation of metal cations.

In preparing the precursors following the method of the aforesaid prior patent application, a molybdic acid or soluble non-metallic molybdate is combined with a water-soluble acid or non-metallic salt of an element selected from the group consisting of silicon, phosphorus and arsenic in aqueous solution, and then there are added to the mixture an aqueous chloride ion and a compound selected from the group consisting of phosphotungstate, silicotungstate, vanadium arsenate, silicoarsenate, phosphovanadate, silicovanadate, corresponding acids thereof or mixtures thereof. The resulting combination is dried and calcined to yield the precursor product having an empirical formula $$Y_wMo_xA_yO_z \quad (I)$$

wherein Y is phosphorus, arsenic, silicon or mixtures thereof,

A is tungsten, vanadium, arsenic (when Y is not arsenic), or mixtures thereof, w ranges from 0.5 to 1.5 x ranges from 10 to 15 y ranges from 0.1 to 2.0 and z is an integer necessary to satisfy the valency requirements of the formula, ranging from 1 to 42.

Higher catalytic activity is imparted to the precursor products if one or more metallic cations are incorporated during the chloride ion stabilization step. Such metallic cation can be selected from the group consisting of aluminum, antimony, barium, bismuth, cadmium, calcium, cerium, chromium, cobalt, copper, iron, lanthanum and other rare earths, lead, magnesium, manganese, nickel, potassium, rhenium, rhodium, ruthenium, silver, strontium, thallium, titanium, zinc, zirconium, and mixtures thereof.

The non-metallic molybdate salts used in the catalyst precursor preparation include ammonium molybdate $[(NH_4)_2MoO_4]$ and ammonium heptamolybdate $[(NH_4)_6Mo_7O_{24}.4H_2O]$, molybdic acid, molybdic oxide and molybdenum trioxide. For the preparation of precursors containing cations in addition to the molybdates salts referred to above, any metallic molybdate can be used such as barium molybdate, calcium molybdate, iron molybdate, lead molybdate, potassium molybdate and strontium molybdate. It is critical when the metallic molybdate salts are employed that the final precursor has a total metal cation to molybdenum ratio in the range of about 1:10 to about 1:13.

The compound of silicon, phosphorus or arsenic for the preparation of the precursor an be an acid or a non-metallic silicate, phosphate or arsenate such as ammonium silicate, ammonium phosphate, ammonium arsenate, phosphoric acid, orthoarsenic acid, metaarsenic acid, pyroarsenic acid, arsenous oxide, arsenous hydride, hypophosphoric acid, metaphosphoric acid, orthophosphoric acid, pyrophosphoric acid, orthophosphorous acid, and pyrophosphorous acid.

The chloride ion stabilization (CIS) step takes place in the presence of concentrated hydrochloric acid or other material such as an aqueous solution of ammonium chloride having a high concentration of chloride ions at temperatures in the range of 20° to 80° C. In the case of the metal cation-containing precursor, all or a part of the chloride ion can come from the chloride of one or more of the cations incorporated into the catalyst during this CIS step.

The presence of the chloride ion is critical for the uniform formation of the active molybdenum species and to avoid the conflicting influence that pH tends to have on the aqueous solution during the method of preparing the precursor. The preferred results are obtained when the chloride ion is present in the CIS step in the ratio of one equivalent of chloride ion to one equivalent of molybdenum, but the chloride can range in concentration as high as five equivalents per equivalent of molybdenum. Although most, if not all of the optional metal cation is incorporated into the precursor during the CIS step, the cations can also be added with the molybdate salts as discussed above.

A suitable form of the metal cation that can be incorporated into the precursor if desired, includes the halides, oxides, nitrates, ammonium salts, hydroxides, acetates, carbonates, sulfates and the like. A particularly useful form is the chloride of Al, Sb, Ba, Bi, Cd, Ca, Ce, Cr, Co, Cu, Fe, La, Pb, Mg, Mn, Ni, Nd, K, Pr, Re, Rh, Ru, Ag, Sr, Tl, Ti, Zn, Zr, and mixtures thereof. The total metal cation to molybdenum ratio should be in the range of 1 mole cation to about 10 gram atoms molybdenum to 1 mole cation to about 13 gram atoms molybdenum.

The empirical formula for the precursor containing the metal cation is $$X_u Y_w Mo_x A_y O_z$$

wherein X is one of the metal cations listed above, or mixtures of these;
u ranges from 0.5 to 2.0; and
Y, A, w, x, y and z are the same as that set forth above in formula (I).

The tungsten, vanadium, arsenic, or mixtures of elements are present in the precursor, preferably so that the mole ratio is 0.25 to 2.0 moles to about 12 moles molybdenum. The best results are obtained where the elements are incorporated into the catalyst in an aqueous solution of phosphotungstate, phosphotungstic acid or similar heteropoly anion-containing compounds.

When the CIS step is not followed or when the raw materials exceed the mole limits given, inactive molybdenum species are formed in solution. It has been found that when the chloride ion is not present, the molybdenum species may exist in solution in different inactive forms rather than being present as the active molybdate anion. The presence of chloride ion also maintains the molybdenum species in a very highly complexed form, which is the active species. For example, the addition of the preferred phosphorus element creates the active phosphomolybdate anion in solution, and the chloride ion stabilizes this anion during the remaining steps of the precursor preparation. The most preferred results are obtained when molybdenum is present as the 12-phosphomolybdate anion. However, similar results are obtained from isomorphous heteropoly silicomolybdates, arseno molybdates or mixtures thereof.

The foregoing method of preparation using the ratios of the raw materials set forth above prevents the formation of other molybdenum species which are structurally different and not active for the oxidation of carboxylic aldehydes to the acids. This method also prevents the formation of inactive molybdenum trioxide species during the drying and calcination steps, and thereby gives the highly pure and substantially active molybdenum species. By maintaining the structural purity, one obtains as precursor an excellent initial catalyst with improved activity, selectivity and stability.

The addition of the optional metal cations in the ratio set forth above also prevents the formation of less selective regular molybdates, and also results in the elimination of excess metal oxides in the catalyst. In either case, the formation of precursors and catalysts having low stability is avoided.

The prior art shows that the the molybdenum compounds and other metal oxides tend to catalyze reactants and to total combustion and to form oxygenated products which tend to decrease the selectivity to, for example, acrylic and methacrylic acids and to decrease the structural stability of the catalysts. Therefore, the formation of metal oxides and such molybdenum compounds must be avoided.

Preferably, phosphotungstic acid is employed in the formation of the precursors prepared by the described method in the ratio 0.5–1.0 moles per mole of molybdenum to form the isomorphous phosphotungsto molybdate anion. Using these small ratios, the phosphotungstic acid helps to form the most active distorted phosphomolybdate anion having a very stable structure and a structure which is resistant to deterioration.

After the chloride ion stabilization step, the resulting mixture is dried at temperatures of 75° to 150° C., and the dried product is calcined in air at temperatures from 150° to 500° C., preferably 200° to 420° C. for a period of 1 to 48 hours. The calcined product can then be ground to increase its surface area to a range of 35 to 100 mesh having a surface area of 0.1 to 50 m²/g.

If desired, the catalyst precursor can be supported on any known carrier such as silica, alumina, Alundum, zeolites, graphite, pumice, silicon carbide, zirconia, titania or other inert carrier. The precursor products used in the method of the present invention can be coated onto or otherwise incorporated in the carrier in the range of about 10 to 100% by weight based on the weight of the carrier. This can be accomplished by any of the various means well-known to those skilled in the art.

The precursors of the present invention can be used as catalysts to oxidize unsaturated aldehydes such as acrolein and methacrolein in the presence of molecular oxygen to yield acrylic acid and methacrylic acid, respectively. The oxygen may be in the form of pure oxygen, oxygen diluted with inert gases, air with or without additional oxygen. The oxidation reaction can be in either a fixed or fluidized catalyst bed at temperatures in the range of 200° to 475° C., preferably from 250° to 375° C., pressures from 0.5 to 50 atmospheres, preferably 1 to 10 atmospheres absolute. The residence time of the reactants in the presence of such catalyst ranges from 0.2 to 30 seconds, preferably from 1 to 20 seconds. The ratio of oxygen to unsaturated aldehydes in the feed gas ranges from 1:1 to 10:1, preferably from 1:1 to 3.1.

Preferably, steam is added to the gaseous reaction mixture to improve the yield of unsaturated carboxylic acids from the aldehydes. Helium, nitrogen, saturated hydrocarbons such as methane, propane, butane or the like, or other inert gases can also be added to the gaseous reactant mixture. The concentration of steam ranges from 2 to 80%, preferably from 10 to 50% of the volume of the feed.

In addition to the production of unsaturated carboxylic acids, the precursors can also be employed in the oxidation of unsaturated monoolefins such as propylene and isobutylene to the corresponding unsaturated acid and/or aldehydes such as acrylic and methacrylic acid and acrolein and methacrolein. A preferred reaction mixture for the oxidation of monoolefins comprises one mole of olefin to 1.5 to 3 moles of molecular oxygen and 0.5 to 20 moles of water in the form of steam. The reaction takes place at temperatures in the range of 300° to 500° C., preferably 360° to 450° C., 1 to 10 atmospheres, preferably 1 to 2 atmospheres absolute and a residence time of 0.1 to 10, preferably about 0.5 to 3 seconds.

The method for preparation of the described precursors can also be extended to prepare other molybdate catalysts which are useful in a wide variety of other chemical processes including dehydrogenation, ammoxidation and dehydrocyclization.

The following examples illustrate embodiments for preparation of precursors useful in practice of the present invention. It is to be understood, however, that these are for illustrative purposes only and are not intended to be wholly definitive as to the operating conditions and scope for the preferred practice of the methods of the present invention.

EXAMPLE 1

A quantity of 210.0 grams of ammonium molybdate was dissolved in 600 ml. of water. 13.2 grams of diammonium phosphate were dissolved in 100 ml. of water and then added to the ammonium molybdate solution. During the chloride ion stabilization (CIS) step, 25 cc of concentrated hydrochloric acid and 20 grams of phosphotungstic acid dissolved in 15 ml. of water were added to the aqueous solution of reactants. The mixture was then dried at 85° C. and calcined at 350° C. for 6 hours. Under these conditions, the resulting composition was found to be essentially free of chloride ion by elemental analysis. The presence of the chloride ion is believed to be detrimental to the catalyst activity.

The resulting precursor product had an empirical formula as follows:

$$P_{1.09}Mo_{12}W_{0.9}O_z$$

where z is a integer to meet the valency requirements of the formula.

The precursor material was then ground to a uniform particle size in the range of from about 500 to 600 microns. The precursor was subjected to infrared spectroscopy, X-ray diffraction and surface acidity measurements. From these characterization methods, it was confirmed that the active component therein is a distorted phosphomolybdate anion. In addition, it was confirmed that no other molybdates or molybdenum trioxide compounds were present.

To test catalytic activity of the obtained precursor it was placed in a fixed bed, stainless steel reactor 18 inches (46 cm.) in length and 5/8 inch (1.65 cm.) inside diameter. The reactor was inserted to a length of 12 inches (30 cm.) in a heated zone to convert methacrolein to methacrylic acid under the following reaction conditions to achieve the following results:

| Feed: | Methacrolein 4.1% | Oxygen 8.35% | Steam 12.5% | Helium 75.0%* |
|---|---|---|---|---|

Temperature: 320° C.
Pressure: Atmospheric
Residence Time: 1.32 seconds
Space Velocity: 2730 hr.$^{-1}$ Conversion, mole %: $\frac{\text{Total reacted methacrolein}}{\text{Methacrolein in the feed}} \times 100 = 84.1\%$

*By volume
Selectivity of Methacrylic Acid, mole %:

$\frac{\text{Methacrylic acid formed}}{\text{Total reacted methacrolein}} \times 100 = 87.0\%$ Selectivity of Acetic Acid, mole %:

$\frac{\text{Acetic acid formed}}{\text{Total reacted methacrolein}} \times 100 = 8.6\%$

EXAMPLE 2

The catalyst preparation procedure of Example 1 was followed to yield a catalyst precursor having the following structural formula:

$$P_{1.12}Mo_{12}W_{1.2}O_z$$

This product was tested under exactly the same oxidation conditions as the product of Example 1. The resulting conversion to methacrylic acid was 83.3% and the selectivity of methacrylic acid was 87.2% and of acetic acid was 9.2%.

EXAMPLE 3

The Example 1 product preparation procedure was again followed to yield a product having the following formula:

$$P_{1.18}Mo_{12.0}W_{1.8}O_z$$

This product was tested under the same conditions that were followed in Example 1 to produce methacrylic acid. The precursor product showed an 80.1% conversion and a selectivity of methacrylic acid equal to 82.7%, and of acetic acid equal to 12.1%.

The foregoing data of Examples 1-3 illustrates that even without the addition of a metal cation during the formation of the precursor the oxidation activity was very high even when compared to prior art catalysts which contain one or more metal cations.

EXAMPLE 4

The procedure of Example 1 was generally followed except that the CIS step was varied to illustrate the improvement one can make in the already high activity of the precursors by the incorporation of at least one metal cation.

During the CIS step, 22.6 grams of antimony trichloride were dissolved in 6 cc of concentrated hydrochloric acid and diluted with 20 cc water. This solution was added to the aqueous solution resulting from a combination of the ammonium molybdate and diammonium phosphate. 15 grams of phosphotungstic acid dissolved in 50 ml. water were then added to the mixture and the slurry was dried to 85° C. and calcined at 350° C. for 6 hours. The empirical formula of the product is set forth in Table I below.

After the precursor was ground to reduce the size to about 560 microns, the oxidation reaction of Example 1 was followed to convert methacrolein to methacrylic acid except that the temperature was lowered from 320° C. to 304° C. and the residence time was increased from 1.32 to 3 seconds (1200 hr.$^{-1}$ space velocity). The conversion was 89.0% with a selectivity of methacrylic acid equal to 96.2% and of acetic acid equal to only 0.98%.

EXAMPLE 5

The procedure of Example 4 was followed except that during the CIS step in place of the 22.6 grams of antimony trichloride were added to a mixture of 26.1 grams of lead nitrate and 6.5 grams of cobalt nitrate. The resulting product was reacted under the same oxidation conditions of Example 4 to achieve the results set forth in Table I below.

EXAMPLE 6

The procedure of Example 4 was generally followed except for the following modifications. During the CIS step, 14.5 grams of lead nitrate and 7.5 grams of cobalt nitrate were dissolved in 6 cc of concentrated hydrochloric acid and diluted with 20 cc water. 30 grams of phosphotungstic acid dissolved in 50 ml. water were added to the mixture of lead nitrate, cobalt nitrate, ammonium molybdate and diammonium phosphate already combined and in solution. The results of this product when tested as catalyst in the oxidation of methacrolein under the Example 4 conditions are also given in Table I below.

EXAMPLE 7

The procedure of Example 6 was followed except that in place of the 14.5 grams of lead nitrate and 7.5 grams of cobalt nitrate were added, 7.5 grams of barium nitrate, 8.3 grams of lead nitrate, 3.5 grams of cobalt nitrate and 7.5 grams of strontium nitrate. The results of the use of this product as catalyst in the oxidation of methacrolein under the Example 4 conditions are set forth in Table I below.

In all of the procedures described in Examples 4–7, the metal cation to molybdenum ratio was 1:12.

CONTROL 1

A control catalyst was prepared using the procedure of Example 4 except that the step of incorporating 20 grams of phosphotungstic acid was eliminated. The catalyst was employed in the oxidation of methacrolein using the same conditions as Example 4. The results are also given in Table I below.

EXAMPLE 8

This example illustrates the unique properties of the CIS method employed in producing a precursor of high activity for oxidizing acrolein to acrylic acid under the identical conditions described in Example 4. The conversion of acrolein to acrylic acid using the same $Sb_1P_{1.09}Mo_{12}W_{0.9}O_z$ catalyst of Example 4 was 89.6% conversion and a selectivity of acrylic acid equal to 88.8% and of acetic acid equal to 6.2% were obtained.

The foregoing examples clearly illustrate the extraordinary characteristics of these products which contain the essentially pure and stable phosphomolybdate anion as determined by their activity in oxidizing unsaturated aldehydes to the corresponding carboxylic acids.

PREFERRED EMBODIMENTS OF THE PRESENT INVENTIONS

The starting material for preparation of the highly active and selective catalysts of the present invention is

TABLE I

| EXAMPLE | PRODUCT | CONV. | SELECTIVITY METHACRYLIC ACID | ACETIC ACID |
|---|---|---|---|---|
| 4 | $Sb_1P_{1.09}Mo_{12}W_{0.9}O_z$ | 89.0% | 96.2% | 0.981% |
| 5 | $Co_{0.21}Pb_{0.78}P_{1.09}Mo_{12}W_{0.9}O_z$ | 76.4% | 77.4% | 8.0% |
| 6 | $Co_{0.5}Pb_{0.5}P_{1.18}Mo_{12}W_{1.18}O_z$ | 64.2% | 95.1% | 1.0% |
| 7 | $Ba_{0.25}Co_{0.25}Sr_{0.25}Pb_{0.25}P_{1.18}Mo_{12}W_{1.18}O_z$ | 60.7% | 90.1% | 1.5% |
| CONTROL | | | | |
| 1 | $Sb_1P_1Mo_{12}O_z$ | 36.8% | Trace | Nil |

Table 1 above illustrates the unexpected results one obtains from the catalyst precursors employed in the method of the present invention which contain the defect heteropoly phosphomolybdate anion compared to the results one obtains from a catalyst containing antimony phosphomolybdate of the type described in the prior art, for example, U.S. Pat. No. 3,965,163. The foregoing results also indicate that the major significant active species in the precursor product employed in making the catalysts of the present invention, is this defect heteropoly phosphomolybdate anion. One is not restricted to the incorporation of any metal cation or any particular composition in the method of preparation of such precursors.

CONTROL 2

A second control catalyst was prepared using the procedure of Example 1 except that no hydrochloric acid or other chloride ion-containing medium was used in the catalyst preparation to obtain a catalyst having the same empirical formula as the product of Example 1, i.e.: $P_{1.09}Mo_{12}W_{0.9}O_z$.

Under the identical oxidation conditions, as described in Example 1, no appreciable reaction of methacrolein to methacrylic acid was observed. The oxidation temperature was then increased to 345° C. Under these conditions, the conversion was 61.7%, and a selectivity of methacrylic acid equal to 45.6% and of acetic acid equal to 17.5% were obtained.

The second control catalyst was subjected to the same characterization methods as the product of Example 1 and showed the presence of considerable amounts of molybdenum trioxide along with phosphomolybdate.

This is believed to be the cause for the poor activity of this control catalyst.

a stable heteropoly molybdate precursor corresponding to formula I or II above and prepared by the method above described employing the chloride in stabilization step. The precursor is employed in already calcined form and further impregnated and treated as hereinafter described.

To obtain the highly active catalysts useful in the conversion of $C_3$ and $C_4$ olefins in a single stage directly to the corresponding unsaturated carboxylic acids, the precursor is treated to incorporate a predetermined amount of one or more Group VIII base metals and with a selenium or tellurium compound, then dried and calcined. The resulting final catalyst has the empirical formula corresponding to one of the formulae IV, V, or VI above.

The starting heteropoly molybdate precursor employed must contain the molybdenum in a well defined defect structure. The subsequent impregnation with the metal cation must be kept within limited ranges to obtain catalyst capable of forming desired amounts (5% or more) of unsaturated acid directly from the olefin. As the amount of incorporated cation is increased, above about 3 moles per 10–12 moles of molybdenum, the yield of unsaturated acid formation from the olefin is decreased and higher aldehyde formation is favored.

Catalysts of substantially the same empirical formula and composition prepared by techniques other than that employed in accordance with the present invention, do not demonstrate the high activity and selectivity as the catalysts of the invention. X-ray analysis of sample catalysts of the invention show the molybdenum to be present as the defect phosphomolybdate anion, while catalysts of the same composition prepared by other methods are found to contain a mixture of different molybdenum species, in which the molybdenum is tetrahedrally and octahedrally surrounded as regular molybdates. Such regular molybdate containing catalysts are less active and less selective in various selective oxidation reactions, than the catalysts made in accordance with the present invention. In addition, catalysts prepared in accordance with the invention have greater structural purity, as identified and confirmed by infrared and X-ray investigations, than hitherto known catalysts. The unusual catalytic properties of the novel catalysts of this invention are believed to result from the fact that the molybdena is present in the heteropoly phosphomolybdate anion state which is much easier to reduce.

Catalysts prepared by the method of the present invention have certain common physical and chemical properties. They have typical infra-red bands at 800 cm$^{-1}$, 970 cm$^{-1}$, 1070 cm$^{-1}$ and 1400 cm$^{-1}$. Their X-ray patterns are substantially identical as well as their surface areas.

Once the primary matrix of the molybdena in the precursor is fixed by following the chloride ion stabilization method, various improved molybdenum catalysts for known petrochemical processes can be prepared therefrom by the described impregnation technique. Thus, catalysts showing excellent performance in conversion of methanol to formaldehyde are obtained by impregnating a preformed primary phosphomolybdate precursor with iron nitrate alone. By impregnating such primary phosphomolybdate precursor with either bismuth nitrate alone or cobalt nitrate alone, catalysts are obtained which show excellent performance in the conversion of olefins to the corresponding aldehydes or nitriles.

Catalysts of the general formula IV to X can also be employed in the conversion of ethyl benzene to styrene, conversion of butene to maleic anhydride, direct oxidation of xylenes to carboxylic acids. The unusual activity of the catalysts is already observed in their ability to produce high yields of acrolein from propylene even in the absence of bismuth therein; the presence of bismuth being reported as essential in certain prior art catalysts designated for use in such conversion of propylene.

In addition to their advantageous use in conversion of olefins to unsaturated carboxylic acids, the catalysts of formulass IV, V and VI find use in the conversion of alcohols to the corresponding aldehydes or acids, the preparation of oxo compounds from the corresponding olefins, and the production of nitriles from the corresponding olefins.

EXAMPLE 9

(a) Formation of catalyst precursor $Ti_2P_2Mo_{20}W_{2.4}O_z$ 354 grams of ammonium molybdate are dissolved in 600 ml water containing 23.0 grams of mono-basic ammonium phosphate. To this solution there is added 20 cc of concentrated hydrochloric acid along with 20.0 ml of titanium chloride. To the obtained mixture there is then added 60.0 grams of ammonium metatungstate and the obtained mixture dried with constant stirring, then calcined at 350° C. for 6 hours.

(b) Preparation of Catalyst $Co_{1.7}Fe_{0.37}Te_{3.1}Ti_2P_2Mo_{20}W_{2.4}O_z$ 50.0 grams of cobalt nitrate, 15.0 grams of iron nitrate and 48.0 grams of tellurium dioxide are added to 150 ml water and then mixed with the precursor (a) above. The obtained product is dried at 120° C. for 6 hours, followed by calcination at 350° C. for 6 hours.

EXAMPLE 10

(a) Formation of Catalyst Precursor $P_{1.6}Mo_{20}O_z$ 177 grams of ammonium molybdate and 9.5 grams of mono-basic ammonium phosphate are dissolved in 400 ml water. To this solution there is added 20 cc of concentrated hydrochloric acid and the obtained product dried with constant stirring, then calcined at 350° C. for six hours.

(b) Preparation of catalyst $Co_{2.0}Se_{2.0}Fe_{0.6}P_{1.6}Mo_{20}O_z$

A solution of 29.1 grams of cobalt nitrate, 12.0 grams of iron nitrate and 12.90 grams of selenious acid in 100 ml water, is mixed with the above precursor (a) and dried at 120° C. for 6 hours, then calcined at 350° C. for 6 hours.

(c) Preparation of Catalyst $Co_{2.0}Te_{3.0}Fe_{0.3}P_{1.6}Mo_{20}O_z$ 29.1 grams of cobalt nitrate, 6.0 grams iron nitrate and 24.0 grams of tellurium dioxide are added to 120 ml water, and mixed with the above precursor (a). The mixture is dried at 120° C. for 6 hours, followed by calcination at 350° C. for 6 hours.

EXAMPLE 11

(a) Formation of catalyst precursor $Si_1P_1Mo_{10}W_{1.0}O_z$

By the procedure outlined in Example 10(a) above there are combined:

|  | Grams |
| --- | --- |
| Ammonium molybdate | 177 |
| Mono basic ammonium phosphate | 11.5 |
| Silicic acid | 12.0 |
| Ammonium metatungstate | 25.0 | followed by drying and calcining as before.

(b) Preparation of catalyst $Co_{1.0}Te_{1.0}Fe_{0.2}Si_1P_1Mo_{10}W_{1.0}O_z$

The above precursor (a) is admixed with an aqueous solution comprising:

|  | Grams |
| --- | --- |
| Cobalt nitrate | 29.1 |
| Iron nitrate | 8.0 |
| Tellurium dioxide | 16.0 | in 120 ml water; and the mixture dried and calcined as set out in Example 10(b).

EXAMPLE 12

(a) Formation of catalyst precursor $Sb_{0.5}P_{0.55}Mo_{9.7}W_{0.5}O_z$

By the same procedure set out in Examples 10 and 11 above, there is combined:

|  | Grams |
| --- | --- |
| Ammonium molybdate dissolved in 400 ml water | 171.0 |
| Diammonium phosphate | 6.6 |
| Antimony trichloride in 20 cc conc. hydrochloric acid | 11.3 |

-continued

| | Grams |
|---|---|
| Phosphotungstic acid in 20.0 ml water | 10.0 | followed by drying and calcining as before.

(b) Preparation of catalyst
$Bi_{5.0}Fe_{2.87}Sb_{0.5}P_{0.55}Mo_{9.7}W_{0.5}O_z$ The dried and calcined precursor of (a) above is added to a solution of:

| | Grams |
|---|---|
| Bismuth nitrate dissolved in 50 ml conc. $HNO_3$ | 242.0 |
| Iron nitrate dissolved in 50 ml water | 115.0 |

The product is dried and calcined as in previous example 11(b).

EXAMPLE 13

(a) Formation of catalyst precursor $P_{1.1}Mo_{12.0}W_{1.0}O_z$

Following the procedures of Examples 10(a) to 12(a) above, a dried and calcined product is prepared from:

| | Grams |
|---|---|
| Ammonium molybdate dissolved in 400 cc water | 212 |
| Diammonium phosphate dissolved in 20 cc conc. HCl | 6.6 |
| Phosphotungstic acid | 20 | followed by drying and calcining.

(b) Preparation of catalyst $Co_{5.0}Fe_{0.5}P_{1.1}Mo_{12.0}W_{1.0}O_z$

The calcined precursor (a) above is admixed with a solution in 200 ml water of:

| | Grams |
|---|---|
| Cobalt nitrate | 145.5 |
| Iron nitrate | 20.2 | and the obtained product dried and calcined as in Examples 10(b) to 12(b) above.

Catalysts of Examples 9(b) through 13(b) tested in conversion of propylene under the following reaction conditions:

| | Propylene | Oxygen | Steam | Helium |
|---|---|---|---|---|
| Feed (vol %) | 5.9 | 13.1 | 11.0 | 70.0 |
| GHSV at room temperature | 1350 | | | | obtain results shown in Table 1 below compared to control catalysts.

Conversion Mole % = $\frac{\text{Total reacted } C_3 \text{ olefin}}{C_3 \text{ olefin in feed}} \times 100$ Selectivity Mole % = $\frac{\text{acrolein or acrylic acid formed}}{\text{Total propylene reacted}} \times 100$

TABLE 1

| | | SELECTIVITY | | | |
|---|---|---|---|---|---|
| Catalyst | Temp °C. | Conv. % | Acrylic Acid % | Acrolein % | Acetic Acid % |
| Example 9(b) | 416 | 98.5 | 18.9 | 44.77 | 6.2 |
| Example 10(b) | 400 | 71.6 | 5.9 | 40.74 | 7.78 |
| Example 10(c) | 433 | 86.7 | 26.09 | 68.12 | 1.52 |
| Example 11(b) | 450 | 71.7 | 37.23 | 48.8 | 3.20 |
| Example 12(b) | 400 | 76.5 | 1.21 | 76.28 | — |
| Example 13(b) | 400 | 92.5 | Trace | 94.21 | — |
| Control 3 | 425 | 25.1 | 1.21 | 40.50 | — |
| Control 4 | 430 | 36.2 | 1.7 | 40.1 | — |

Among examples of other catalysts of the empirical formulae IV, V, VI, which are prepared by the methods of Examples 9 to 11, and which are useful in conversion of $C_3$ and $C_4$ monoolefins, are:

$Sn_2Fe_1Te_{0.5}P_1Mo_{10}W_1O_z$ (VII)

$Mn_2Fe_1Te_{0.5}P_1Mo_{10}W_1O_z$ (VIII)

$Co_1Mn_1Fe_1Mg_{0.5}Te_{0.5}P_1Mo_{10}W_1O_z$ (IX)

$Co_2Fe_{0.5}Mg_{0.5}Te_1P_{0.5}Si_{0.5}Mo_{10}W_1O_z$ (X)

For the preparation of a control catalyst, the chloride ion stabilization technique (CIS) was not employed. The resulting catalyst obtained considerably lower total conversion of propylene and produced only very small amounts of acrylic acid even at higher temperatures than need be employed for the preferred catalysts prepared from precursors obtained with the CIS technique.

EXAMPLE 14

Preparation of Control Catalyst $Mn_2Bi_{1.0}Fe_{1.0}Sb_{1.0}Co_{0.8}P_1Mo_{12}O_z$ To a solution comprising 106 grams ammonium molybdate and 5.8 grams monobasic ammonium phosphate, there was added: 90.0 grams of cobalt nitrate in 150 ml water; 11.3 grams antimony trichloride in 10 cc concentrated hydrochloric acid; 24.0 grams of bismuth nitrate in 5 cc concentrated nitric acid and 20 cc water; 20.0 grams manganese chloride in 20 cc water and a slurry of precipitated iron hydroxide from 20.0 grams of iron nitrate. Drying and calcining was as in previous Example 10(b).

The infrared spectrum (I.R.) of the above catalyst showed the presence of typical heteropoly phosphomolybdate anion, as an admixture of regular molybdates. Hence there was no stabilization of the active heteropoly phosphomolybdate structure. By the regular hitherto known methods only a mixture of regular metal molybdates are obtained which are less active and less selective than the catalytic products obtained in accordance with the present invention. The poorer activity of such catalysts in conversion of propylene are observed from Table 1 above.

EXAMPLE 15

Preparation of Control Catalyst $Bi_{5.0}Fe_{2.87}Sb_{0.5}P_{0.5}Mo_{9.7}W_{0.5}O_z$ This catalyst was prepared using the same amount of the chemicals as in preparation of the catalyst of Example 12(b), but not using the chloride ion stabilization technique. The method employed was as follows:

To 171.0 grams of ammonium molybdate dissolved in 400 ml water there was added 6.6 grams of diammonium phosphate. The obtained solution was admixed with a composition prepared from:

242.0 grams of bismuth nitrate in 50 cc concentrated nitric acid and 60 cc concentrated hydrochloric acid in 300 ml water;

115.0 grams ferric nitrate dissolved in 400 ml water and precipitated as iron hydroxide by reaction with ammonium hydroxide;

11.3 grams of antimony trichloride in 10 cc concentrated hydrochloric acid; and 10.0 grams of phosphotungstic acid dissolved in 20 ml water.

The obtained slurry was dried and calcined as in previous Example 10(b).

The obtained calcined catalyst showed poor activity and selectivity in conversion of propylene at 430° C., as seen in Table 1.

EXAMPLE 16

Preparation of Control Catalyst $Co_{2.0}Te_{3.0}Fe_{0.3}P_{1.5}Mo_{20}O_z$

A catalyst similar in composition to that of Example 10(c) above was prepared by the hitherto known regular precipitation method, without use of a precursor stabilized by the chloride ion stabilization technique of the invention. The method employed was as follows:

177.0 grams of ammonium molybdate were dissolved in 600 ml water with 9.5 grams of monobasic ammonium phosphate. To this solution was added:

29.1 grams of cobalt nitrate dissolved in 20 ml water;

24.0 grams of tellurium dioxide;

6.1 grams of iron nitrate dissolved in 10 ml water.

The obtained slurry was dried and calcined as in Example 10(b) above.

The calcined catalyst had poor activity and selectivity. The infrared pattern indicated the presence of mixtures of various molybdates and metal oxides. At a temperature of 430° C. total conversion of propylene was 48.7% at selectivities of 47.2% to acrolein and 1.7% to acrylic acid.

What is claimed:

1. The method of preparing heteropoly molybdate catalysts which comprises impregnating a catalytically active calcined precursor material containing molybdenum in the anion stabilized in defect state, with at least one metallic element, then drying and calcining the impregnated material; said precursor material being one prepared by adding to a compound selected from the group consisting of phosphomolybdates, silicomolybdates and arsenomolybdates, an aqueous chloride ion and a compound selected from the group consisting of phosphotungstates, silicotungstates, vanadium arsenate, silicoarsenate, phosphovandate, silicovandate, the corresponding acids and mixtures thereof.

2. The method as defined in claim 1 wherein said heteropolymolybdate is one corresponding to the empirical formula $Y_wMo_xA_yO_z$ wherein Y is phosphorus, arsenic, silicon or mixtures thereof;

A is at least one element from the group consisting of tungsten, vanadium, or arsenic when Y is not arsenic, w ranges from 0.5 to 1.5 x ranges from 10 to 15 y ranges from 0.1 to 2 z ranges from 1 to 42 and is an integer necessary to satisfy the valency requirements of the formula.

3. The method as defined in claim 2 wherein said impregnated metallic element is a Group VIII base metal.

4. The method as defined in claim 2 wherein said precursor material is admixed in dry form with an oxide of tellurium or selenium or mixtures of these, and treated with an aqueous salt solution of cobalt, iron or both of these salts.

5. The method as defined in claim 2 wherein said precursor material is one obtained by incorporating a salt during the aqueous chloride ion addition, said salt being that of an element selected from the group consisting of Al, Sb, Ba, Bi, Cd, Ca, Ce, Cr, Co, Cu, Fe, La, Pb, Mg, Mn, Ni, Nd, K, Pr, Re, Rh, Ru, Ag, Sr, Tl, Ti, Zn, Zr, and mixtures thereof.

6. The method as defined in claim 2 wherein A is phosphorus.

7. The method as defined in claim 6 wherein said precursor is admixed with an oxide of tellurium or selenium or mixtures of these, and with an aqueous salt solution comprising cobalt, iron or both of these salts.

8. The method as defined in claim 1 wherein the precursor material is one corresponding to the empirical formula $X_uY_wMo_xA_yO_z$ wherein X is an element selected from the group consisting of Al, Sb, Ba, Bi, Cd, Ca, Ce, Cr, Co, Cu, Fe, La, Pb, Mg, Mn, Ni, Nd, K, Pr, Re, Rh, Ru, Ag, Sr, Tl, Ti, Zn, Zr and mixtures thereof;

Y is phosphorus, arsenic, silicon, or mixtures thereof,

A is at least one element from the group consisting of tungsten, vanadium, or arsenic when Y is not arsenic, u ranges from 0.5 to 2.0, w ranges from 0.5 to 1.5, x ranges from 10 to 15, y ranges from 0.1 to 2.0, and z ranges from 1 to 42 and is an integer necessary to satisfy the valency requirements of the formula.

9. The method as defined in claim 8 wherein Y is phosphorus.

10. The method as defined in claim 1 wherein said precursor is a phosphomolybdate, and is impregnated with an aqueous mixture comprising tellurium dioxide and soluble salts of iron and cobalt.

11. The method as defined in claim 10 wherein the precursor material corresponds to the empirical formula $P_{1.6}Mo_{20}O_z$ wherein z represents the residual valence to satisfy the formula; and said aqueous mixture comprises about 2 moles cobalt and 3 moles tellurium per 20 moles of molybdenum present in the precursor.

12. The method as defined in claim 1 wherein said precursor is a phosphomolybdate, and is impregnated with an aqueous solution comprising seleneous acid and soluble salts of iron and cobalt.

13. The method as defined in claim 12 wherein the precursor material corresponds to the empirical formula $P_{1.6}Mo_{20}O_z$ wherein z represent the residual valence to satisfy the formula; and said aqueous impregnating solution comprises about 2 moles of cobalt and about 2 moles of selenium per 20 moles of molybdenum present in the precursor.

14. The method as defined in claim 1 wherein said precursor material corresponds to the empirical formula $Ti_2P_2Mo_{20}W_{2.4}O_z$ wherein z represents the residual valence to satisfy the formula; and is impregnated with an aqueous liquid comprising soluble salts of cobalt and iron and tellurium dioxide.

15. The method as defined in claim 14 wherein said aqueous impregnating liquid comprises about 2–3 moles of cobalt and iron and about 3 moles tellurium per 20 moles of molybdenum present in the precursor.

16. The method as defined in claim 1 wherein said precursor material corresponds to the empirical formula $Si_1P_1Mo_{10}W_{1.0}O_z$ wherein z represents the residual valence to satisfy the formula; and is impregnated with an aqueous liquid comprising soluble salts of iron and cobalt and tellurium dioxide.

17. The method as defined in claim 16 wherein said aqueous impregnating liquid comprises about one mole each of cobalt and tellurium per 10 moles of molybdenum in the precursor.

18. Stable active catalyst containing molybdenum in the anion in defect state comprising a catalytically active precursor surface impregnated with at least on cation from the group consisting of iron and cobalt and with a compound selected from the group consisting of tellurium and selenium.

19. Catalyst as defined in claim 18 wherein said impregnated catalyst is one substantially corresponding to an empirical formula of the group consisting of:

$M_{3-5}R_{2-3}P_{1.5-2.5}Mo_{20}O_z$ $M_{1-3}R_{0.5-2}P_{1-1.5}W_{1-2}Mo_{10}O_z$ $M_{1-2}R_{1-3}P_{2-4}Mo_{20}W_{1-3}O_z$ wherein M comprises one or more metal cations, at least one of which is a base metal cation from Group VIII of the Periodic Table, R is at least one element from the group consisting of selenium and tellurium, and z represents the residual valence to satisfy the formula.

20. Catalyst as defined in claim 19 corresponding to the empirical formula $Co_{1.7}Fe_{0.37}Te_{3.1}Ti_2P_2Mo_{20}W_{2.4}O_z$ wherein z represents the residual valence to satisfy the formula.

21. Catalyst as defined in claim 19 corresponding to the empirical formula $Co_2Se_2Fe_{0.6}P_{1.6}Mo_{20}O_z$ wherein z represents the residual valence to satisfy the formula.

22. Catalyst as defined in claim 19 corresponding to the empirical formula $Co_2Te_3Fe_{0.3}P_{1.6}Mo_{20}O_z$ wherein z represents the residual valence to satisfy the formula.

23. Catalyst as defined in claim 19 corresponding to the empirical formula $Co_1Te_1Fe_{0.2}Si_1P_1Mo_{10}W_1O_z$ wherein z represents the residual valence to satisfy the formula.

* * * * *